United States Patent
Wu et al.

(10) Patent No.: US 12,221,427 B2
(45) Date of Patent: Feb. 11, 2025

(54) PREPARATION METHOD OF (5-FLUORO-2,3-DIHYDROBENZOFURAN-4-YL)METHANAMINE OR ITS SALT, AND INTERMEDIATES THEREOF

(71) Applicants: Ascentage Pharma (Suzhou) Co., Ltd., Suzhou (CN); Ascentage Pharma Group Corp Limited, Hong Kong (CN)

(72) Inventors: Qingquan Wu, Suzhou (CN); Xiuling Wang, Suzhou (CN); Jiawei Wang, Suzhou (CN); Rubin Zhou, Suzhou (CN)

(73) Assignees: Ascentage Pharma (Suzhou) Co., Ltd., Suzhou (CN); Ascentage Pharma Group Corp Limited, Hong Kong (CN)

( * ) Notice: Subject to any disclaimer, the term of this patent is extended or adjusted under 35 U.S.C. 154(b) by 810 days.

(21) Appl. No.: 17/425,817

(22) PCT Filed: May 10, 2021

(86) PCT No.: PCT/CN2021/092728
§ 371 (c)(1),
(2) Date: Jul. 26, 2021

(87) PCT Pub. No.: WO2021/228034
PCT Pub. Date: Nov. 18, 2021

(65) Prior Publication Data
US 2022/0298129 A1    Sep. 22, 2022

(30) Foreign Application Priority Data
May 11, 2020    (WO) ................ PCT/CN2020/089677

(51) Int. Cl.
*C07D 307/79*    (2006.01)
(52) U.S. Cl.
CPC .................. *C07D 307/79* (2013.01)
(58) Field of Classification Search
CPC .................................................. C07D 307/79
See application file for complete search history.

(56) References Cited

U.S. PATENT DOCUMENTS 9,580,437 B2 *    2/2017    Chan ....................... A61P 35/00

FOREIGN PATENT DOCUMENTS

| CN | 110563722 A | 12/2019 |
| CN | 110734436 A | 1/2020 |
| WO | WO 2016103155 A1 | 6/2016 |
| WO | WO 2017221100 A1 | 12/2017 |
| WO | WO 2019120276 A1 | 6/2019 |
| WO | WO 2019158025 A1 | 8/2019 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "Zinc—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*

* cited by examiner

*Primary Examiner* — Nizal S Chandrakumar
(74) *Attorney, Agent, or Firm* — COOLEY LLP; Heidi Erlacher; Xixi Sun

(57) ABSTRACT

The present invention provides a preparation method of (5-fluoro-2,3-dihydrobenzofuran-4-yl)methylamine or a salt thereof, which uses 4-fluoro-3-methylphenol as the starting material, and is carried out through the steps of bromination, O-alkylation, cyclization, bromination, azidation or ammonolysis, and reduction. The reaction route of the present invention has simple synthesis process, convenient operation, high yield, and is environmentally friendly. The prepared (5-fluoro-2,3-dihydrobenzofuran-4-yl)methylamine can be used as an intermediate in pharmaceuticals and fine chemicals.

11 Claims, 7 Drawing Sheets

PREPARATION METHOD OF (5-FLUORO-2,3-DIHYDROBENZOFURAN-4-YL)METHANAMINE OR ITS SALT, AND INTERMEDIATES THEREOF

RELATED APPLICATIONS

This application is a U.S. National Phase application, filed under 35 U.S.C. § 371 (c), of International Application No. PCT/CN2021/092728, filed May 10, 2021, which claims priority to, and the benefit of, International Application No. PCT/CN2020/089677, filed May 11, 2020, the contents of each of which are incorporated by reference herein in their entireties.

TECHNICAL FIELD

The invention belongs to the field of medicine and chemical industry, and particularly relates to a preparation method of (5-fluoro-2,3-dihydrobenzofuran-4-yl)methanamine or its salt, and intermediates thereof.

BACKGROUND (5-fluoro-2,3-dihydrobenzofuran-4-yl)methylamine is an important intermediate compound that can be used to synthesize important drugs and agricultural chemicals. At present, the main literature reports adopt the following route to synthesize and prepare (5-fluoro-2,3-dihydrobenzofuran-4-yl)methylamine:

cyclization reaction would produce positional isomers (A5.2a and A5.2b). Since the positional isomers have the same molecular weight and little difference in polarity, the positional isomer impurities are difficult to remove by purification, and multiple column chromatography separations would be necessary. In addition, zinc cyanide and the catalyst $Pd(PPh_3)_4$ need to be added during the cyanidation process. Zinc cyanide can absorb carbon dioxide in moist air, generate zinc carbonate and release hydrocyanic acid, which is highly toxic and may release toxic gases and vapors during decomposition. The catalyst $Pd(PPh_3)_4$ is also easy to remain. Furthermore, the post-treatments of the four steps in the above route require column chromatography to conduct separation and purification. Therefore, this reaction route is relatively cumbersome, the raw material reagents are highly toxic and expensive, and the post-treatments require multiple column chromatography purifications, so it is not suitable for industrial production.

Therefore, there is an urgent need in the prior art for a preparation method of (5-fluoro-2,3-dihydrobenzofuran-4-yl)methanamine with simple operation, cheap and easy-to-obtain raw materials, environment-friendly and simple post-treatment.

SUMMARY OF THE INVENTION

In view of the above-mentioned problems in the prior art, the present invention provides a preparation method of (5-fluoro-2,3-dihydrobenzofuran-4-yl)methylamine, which

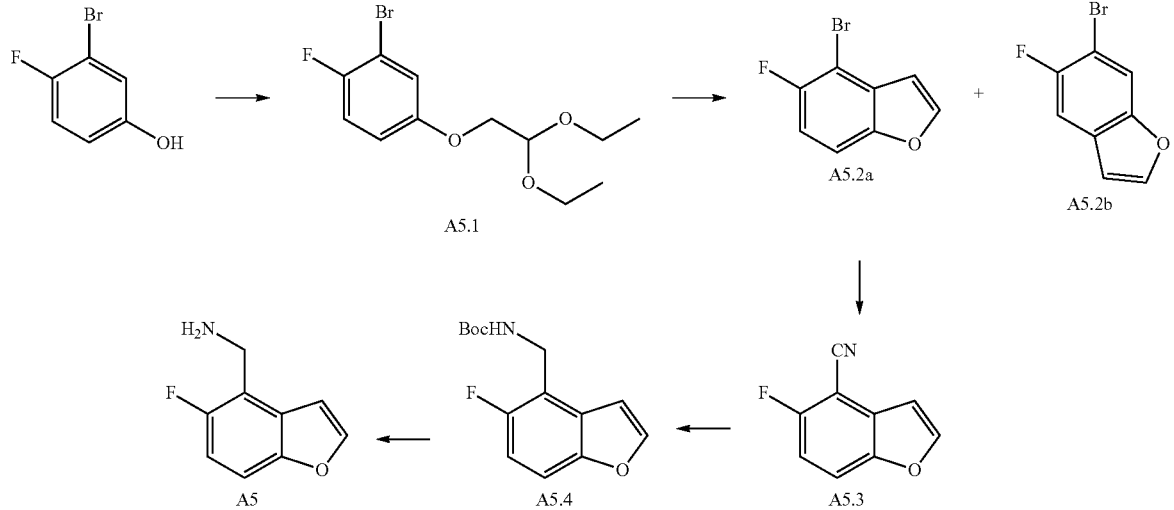

In the above synthetic route, 3-bromo-4-fluorophenol is used as the starting material to react with 2-bromo-1,1-diethoxyethane to obtain 2-bromo-4-(2,2-diethoxyethoxy)-1-fluorobenzene (A5.1), and then PPA cyclization reaction is carried out to obtain 4-bromo-5-fluorobenzofuran (A5.2a and its regioisomer A5.2b), which is then reacted with $Zn(CN)_2$, $Pd(PPh_3)_4$ to obtain 5-fluorobenzofuran-4-carbonitrile (A5.3), and then hydrogenation reduction and amino protection are carried out simultaneously to obtain tert-butyl ((5-fluoro-2,3-dihydrobenzofuran-4-yl)methyl) carbamate (A5.4), and the last step is to remove the amino protecting group to obtain (5-fluoro-2,3-dihydrobenzofuran-4-yl)methylamine (A5). When the inventors reproduced this route, it was found that this route had many defects, for example: the has the advantages of suitable reaction steps, simple operation, low cost and easy availability of reaction raw materials, environmental friendliness, simple post-treatment, and high yield. The overall route of the preparation method can be found in the following Scheme 1 (the following compound numbers refer to the compound numbers listed in Scheme 1):

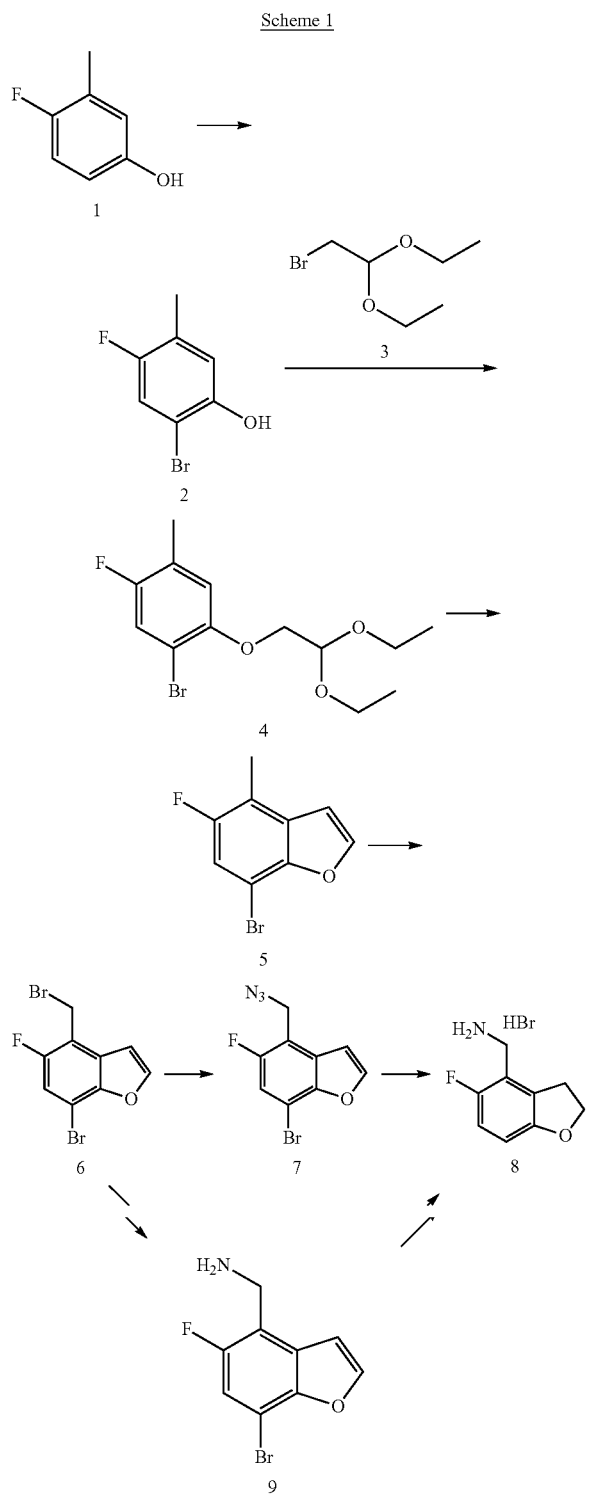

Scheme 1

In one aspect, the present invention provides a preparation method of (5-fluoro-2,3-dihydrobenzofuran-4-yl)methylamine or a salt thereof, which comprises the following reaction steps:

1) Taking 4-fluoro-3-methylphenol (1) as the starting material, and brominating it to obtain 2-bromo-4-fluoro-5-methylphenol (2);

2) Performing O-alkylation reaction between 2-bromo-4-fluoro-5-methylphenol (2) and 2-bromo-1,1-diethoxyethane (3) to obtain 1-bromo-2-(2,2-diethoxyethoxy)-5-fluoro-4-toluene (4);

3) Cyclizing 1-bromo-2-(2,2-diethoxyethoxy)-5-fluoro-4-toluene (4) to obtain 7-bromo-5-fluoro-4-methylbenzofuran (5);

4) Brominating 7-bromo-5-fluoro-4-methylbenzofuran (5) to obtain 7-bromo-4-(bromomethyl)-5-fluorobenzofuran (6);

5) Preparing (5-fluoro-2,3-dihydrobenzofuran-4-yl)methylamine (8) or a salt thereof using the following two-step reaction in any one of 5.1 or 5.2:

5.1) Aziding 7-bromo-4-(bromomethyl)-5-fluorobenzofuran (6) in the presence of an azide to obtain 7-bromo-5-fluoro-4-azidomethyl-benzofuran (7), which is then hydrogenated to obtain (5-fluoro-2,3-dihydrobenzofuran-4-yl)methylamine (8) or a salt thereof; or 5.2) Ammonolyzing 7-bromo-4-(bromomethyl)-5-fluorobenzofuran (6) to obtain 7-bromo-4-(aminomethyl)-5-fluorobenzofuran (9), which is then hydrogenated to obtain (5-fluoro-2,3-dihydrobenzofuran-4-yl)methylamine (8) or a salt thereof.

In one embodiment, the above step 1) is carried out by slowly adding a bromination reagent dropwise to a mixture of 4-fluoro-3-methylphenol (1) and a reaction solvent, and optionally has one or more of the following features:
the reaction temperature is −78° C. to −10° C.;
the bromination reagent is selected from at least one of bromine, phosphorus oxybromide, phosphorus pentabromide, phosphorus tribromide, dibromotrialkylphosphine, dibromodiphenylphosphine, NBS, and dibromohydantoin;
the molar ratio of 4-fluoro-3-methylphenol (1) to the bromination reagent is 1:(1-2);
the reaction solvent is selected from at least one of chlorinated alkanes, ethers, $C_1$-$C_4$ alcohols, acetonitrile, and DMF; and/or
the reaction time is 1-5 h.

In one embodiment, the above step 2) is carried out by performing O-alkylation reaction between 2-bromo-4-fluoro-5-methylphenol (2) and 2-bromo-1,1-diethoxyethane (3) in the presence of a base and a reaction solvent, and optionally has one or more of the following features:
the reaction temperature is 70-150° C.;
the molar ratio of 2-bromo-4-fluoro-3-methylphenol (2) to 2-bromo-1,1-diethoxyethane (3) is 1:(1-2);
the molar ratio of 2-bromo-4-fluoro-3-methylphenol (2) to the base is 1:(1-3);
the base is selected from inorganic base or organic base, and the inorganic base is selected from at least one of sodium hydroxide, potassium hydroxide, sodium carbonate, potassium carbonate, sodium bicarbonate, and potassium bicarbonate; and the organic base is selected from at least one of pyridine, triethylamine, diisopropylethylamine, potassium tert-butoxide, sodium tert-butoxide, sodium methoxide, sodium ethoxide, and DBU;
the reaction solvent is selected from at least one of DMF, acetonitrile, DMSO, toluene or xylene; and/or
the reaction time is 1-20 h.

In one embodiment, the above step 3) is carried out by adding 1-bromo-2-(2,2-diethoxyethoxy)-5-fluoro-4-toluene (4) dropwise to a mixture of polyphosphoric acid and a reaction solvent, and optionally has one or more of the following features:
the reaction temperature is 50-120° C.;
the molar ratio of 1-bromo-2-(2,2-diethoxyethoxy)-5-fluoro-4-toluene (4) to polyphosphoric acid is 1:(1-5);

the reaction solvent is at least one of toluene and xylene; and/or the reaction time is 1-20 h.

In one embodiment, the above step 4) is carried out by brominating 7-bromo-5-fluoro-4-methylbenzofuran (5) in the presence of a reaction solvent, a peroxide initiator and a bromination reagent, and optionally has one or more of the following features:

the reaction temperature is 50-120° C.;

the reaction is carried out in an inert environment, and optionally the inert environment is selected from nitrogen or argon;

the reaction solvent is selected from at least one of chlorinated alkanes, ethers, $C_1$-$C_4$ alcohols, acetonitrile, ethyl acetate, and DMF;

the peroxide initiator is selected from at least one of acyl peroxides, hydroperoxides, dialkyl peroxides, and ester peroxides, and is further preferably selected from benzoyl peroxide, lauroyl peroxide, cumyl hydroperoxide, tert-butyl hydroperoxide, di-tert-butyl peroxide, dicumyl peroxide, tert-butyl peroxybenzoate;, tert-butyl peroxypivalate;

the bromination reagent is selected from at least one of bromine, phosphorus oxybromide, phosphorus pentabromide, phosphorus tribromide, dibromotrialkylphosphine, dibromodiphenylphosphine, NBS, and dibromohydantoin;

the molar ratio of 7-bromo-5-fluoro-4-methylbenzofuran (5) to the peroxide initiator is 1:(0.1-0.5);

the molar ratio of 7-bromo-5-fluoro-4-methylbenzofuran (5) to the bromination reagent is 1:(1-2); and/or the reaction time is 1-20 h.

In one embodiment, the above azidation in step 5.1) is carried out by reacting an azide with 7-bromo-5-fluoro-4-methylbenzofuran (5) in water and a reaction solvent, and optionally has one or more of the following features:

the reaction temperature is 20-80° C.;

the azide is selected from sodium azide or potassium azide;

the molar ratio of 7-bromo-5-fluoro-4-methylbenzofuran (5) to the azide is 1:(1-2);

the reaction solvent is at least one of chlorinated alkanes, ethers, $C_1$-$C_4$ alcohols, acetonitrile, DMF, ethyl acetate, DMSO, and ketone solvents; and/or the reaction time is 1-20 h.

In one embodiment, the above hydrogenation in step 5.1) is carried out by hydrogenating 7-bromo-5-fluoro-4-azidomethyl-benzofuran (7) under pressure in the presence of a catalyst, and optionally has one or more of the following features:

the hydrogen pressure is 0.2-3 Mpa;

the reaction temperature is 40-100° C.;

the reaction solvent is selected from $C_1$-$C_4$ alcohols, ethers, and chlorinated alkanes; and is more preferably selected from methanol or ethanol;

the catalyst is selected from at least one of palladium catalyst or Raney nickel;

the mass ratio of 7-bromo-5-fluoro-4-azidomethyl-benzofuran (7) to the catalyst is (10-50):1; and/or the reaction time is 24-48 h.

In one embodiment, the above ammonolysis in step 5.2) is carried out in an ammonia-alcohol solution, and optionally has one or more of the following features:

the reaction temperature is −30-25° C.;

the reaction solvent is selected from $C_1$-$C_4$ alcohols, and is more preferably selected from methanol or ethanol;

the ammonia concentration in the ammonia-alcohol solution is 5N-10N, or a higher concentration under pressurized conditions; and/or the reaction time is 1-48 h.

The reaction temperature is room temperature or ambient temperature; and/or the reaction time is 1-24 h.

In one embodiment, the above hydrogenation in step 5.2) is carried out by hydrogenating 7-bromo-4-(aminomethyl)-5-fluorobenzofuran (9) under pressure in the presence of a catalyst, and optionally has one or more of the following features:

the hydrogen pressure is 0.2-3 Mpa;

the reaction temperature is 40-100° C.;

the reaction solvent is selected from $C_1$-$C_4$ alcohols, ethers, and chlorinated alkanes, and is more preferably selected from methanol or ethanol;

the catalyst is selected from at least one of palladium catalyst or Raney nickel;

the mass ratio of 7-bromo-4-(aminomethyl)-5-fluorobenzofuran (9) to the catalyst is (10-20):1; and/or the reaction time is 24-48 h.

In one embodiment, the salt of (5-fluoro-2,3-dihydrobenzofuran-4-yl)methylamine is selected from inorganic acid salts and organic acid salts. In one embodiment, the inorganic acid salts are selected from hydrochloride, hydrobromide, hydroiodide, nitrate, sulfate and phosphate, and the like; and the organic acid salts are selected from acetate, propionate, glycollate, 2-hydroxypropionate, pamoate, 2-oxopropionate, oxalate, malonate, succinate, 2-butenedioate, maleate, methanesulfonate, ethanesulfonate, benzenesulfonate and toluenesulfonic acid. In a preferred embodiment, the salt of (5-fluoro-2,3-dihydrobenzofuran-4-yl)methylamine is selected from hydrobromide.

In another aspect, the present invention provides the following compounds: 4-fluoro-3-methylphenol (1), 2-bromo-4-fluoro-5-methylphenol (2), 1-bromo-2-(2,2-diethoxyethoxy)-5-fluoro-4-toluene (4), 7-bromo-5-fluoro-4-methylbenzofuran (5), 7-bromo-4-(bromomethyl)-5-fluorobenzofuran (6), 7-bromo-5-fluoro-4-azidomethylbenzofuran (7) and/or 7-bromo-4-(aminomethyl)-5-fluorobenzofuran (9), and their use as intermediates for the preparation of (5-fluoro-2,3-dihydrobenzofuran-4-yl)methylamine or a salt thereof.

The preparation method of the present invention includes, but not limited to, the following advantages:

1. By performing bromination occupancy at the ortho position of the phenol raw material, the formation of different regioisomer impurities in the subsequent cyclization reaction is avoided, and the post-treatment is simplified while improving the scalability of the process.

2. Avoiding the cyanidation step used in the prior art and the corresponding zinc cyanide reagent and Pd(PPh$_3$)$_4$ catalyst that are expensive, highly toxic and/or difficult to remove, and the reagents and reaction conditions used are environmentally friendly and cheap easy.

3. The post-treatment of each step of the reaction is relatively simple, avoiding tedious procedures such as column chromatography separation, and suitable for industrial production.

DETAILED DESCRIPTION

Figure 1:
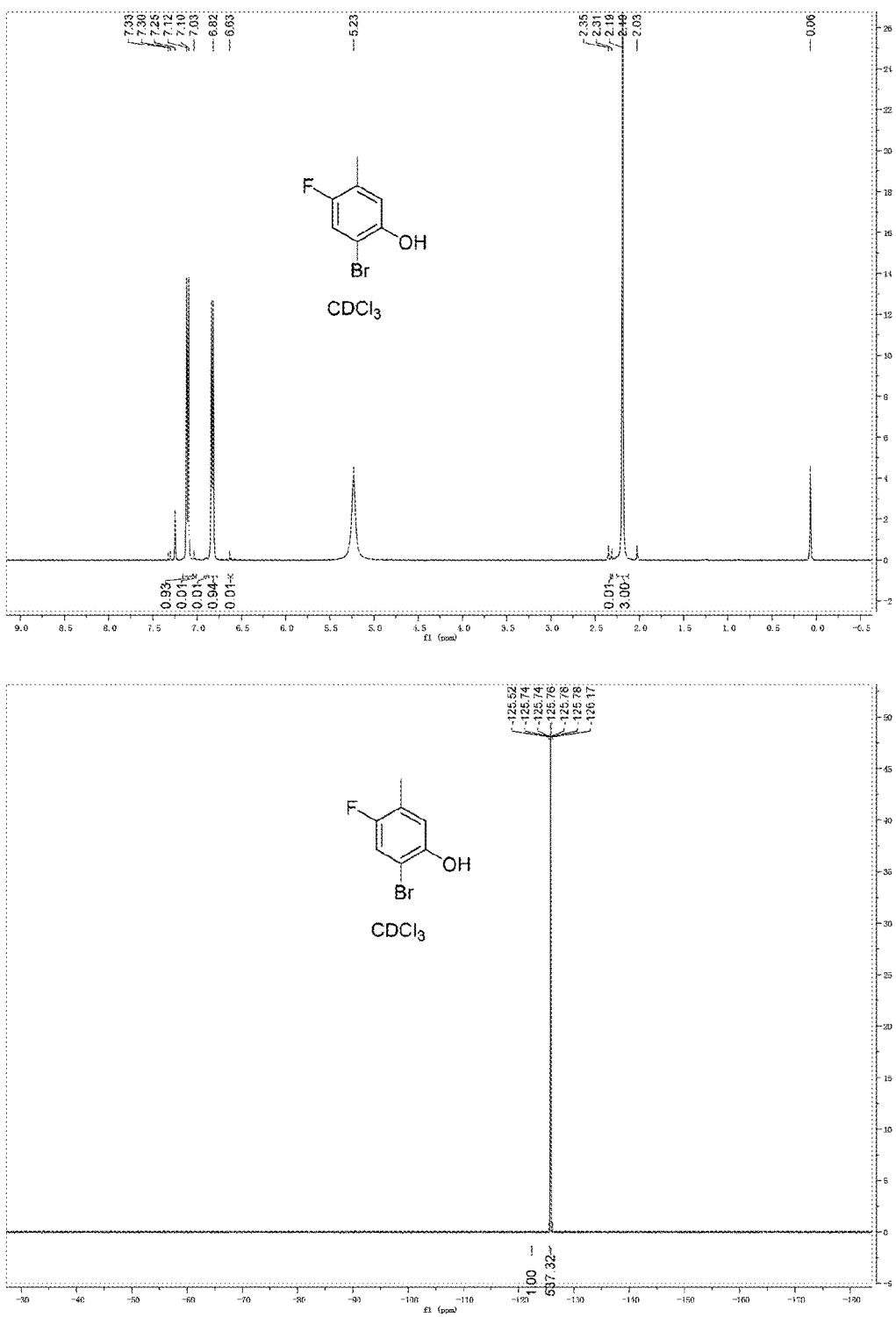
FIG. 1 shows the H-NMR and F-NMR spectrum of 2-bromo-4-fluoro-5-methylphenol (2).
Figure 2:
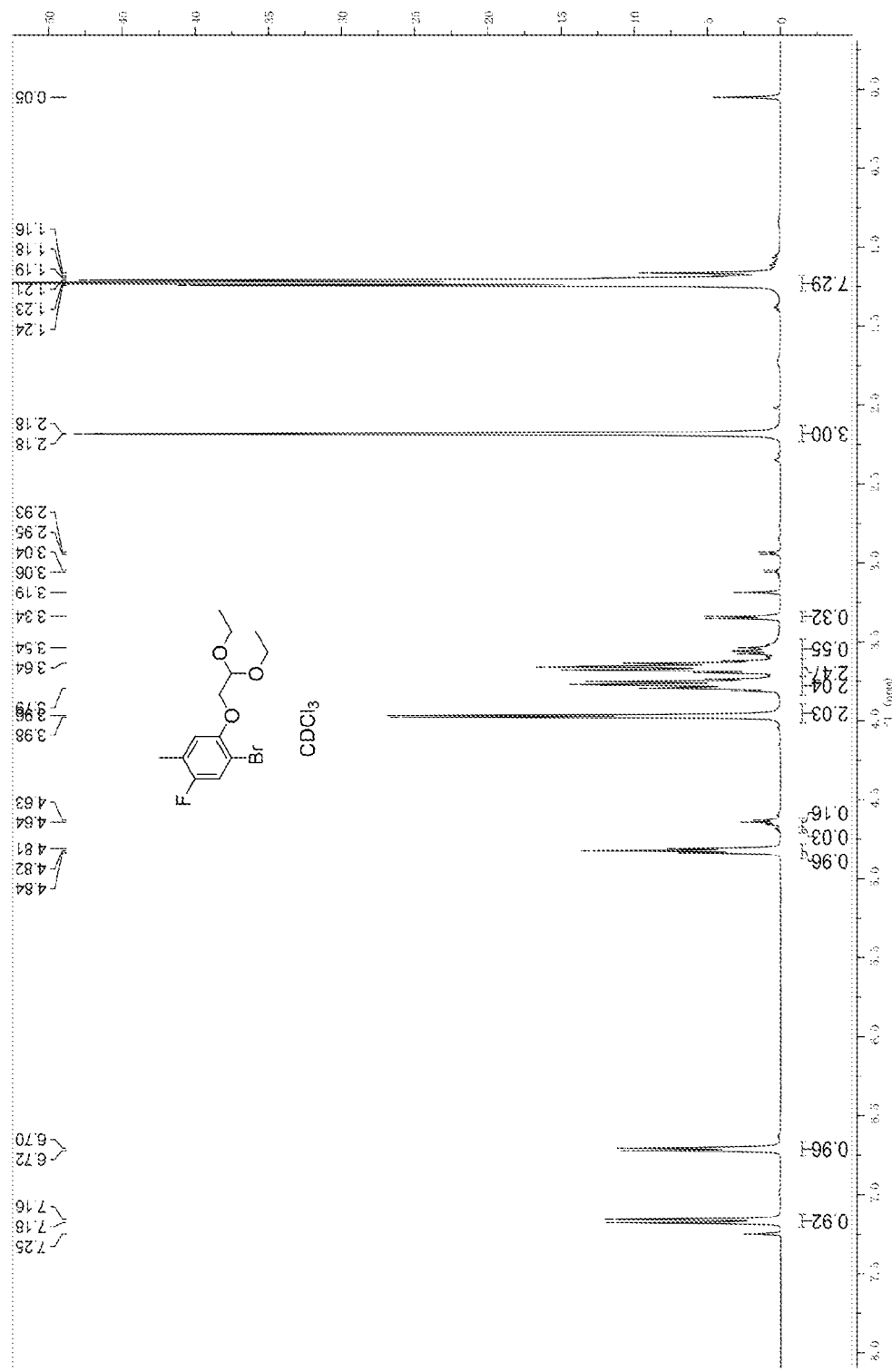
FIG. 2 shows the H-NMR spectrum of 1-bromo-2-(2,2-diethoxyethoxy)-5-fluoro-4-toluene (4).
Figure 3:
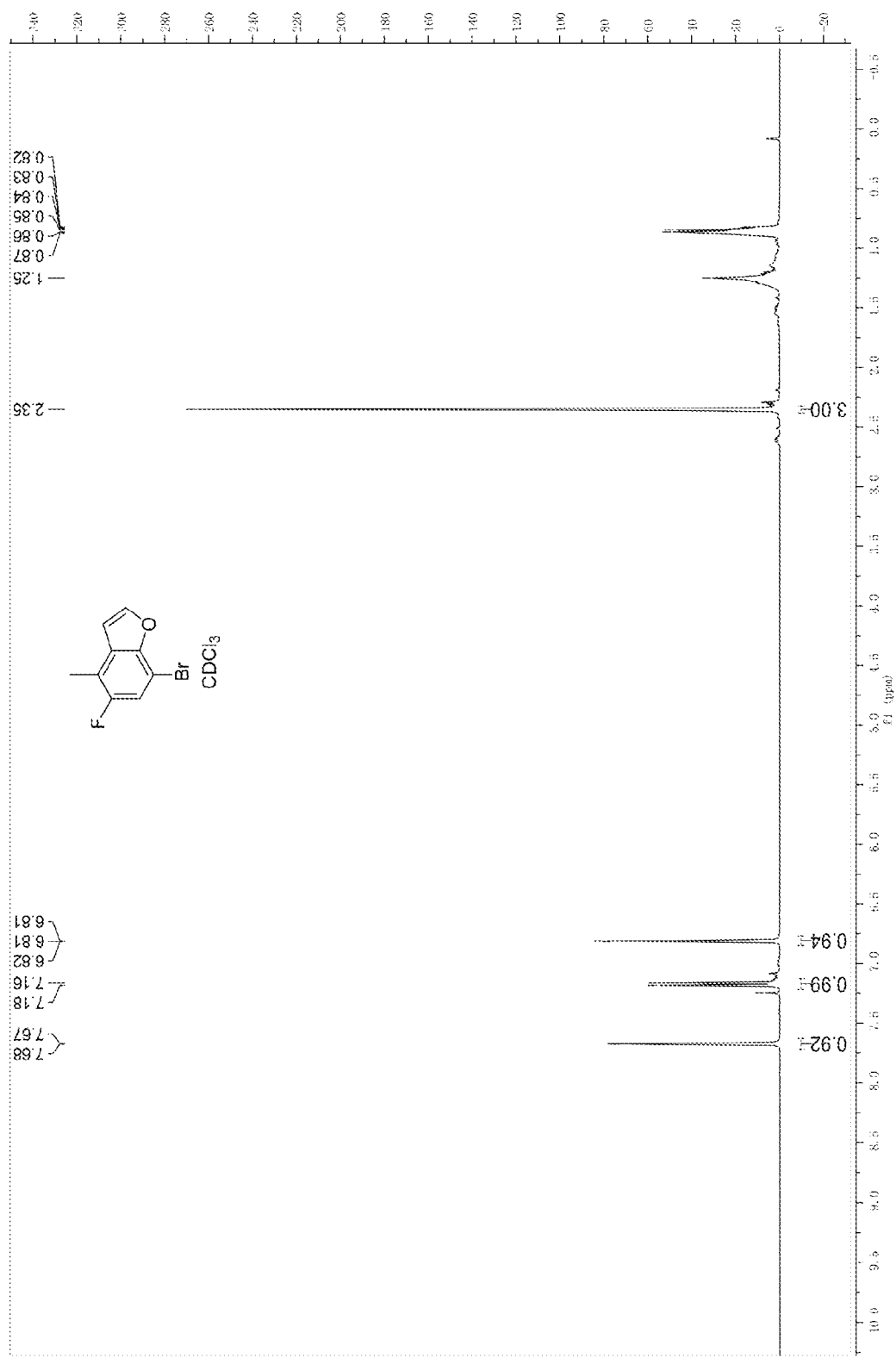
FIG. 3 shows the H-NMR spectrum of 7-bromo-5-fluoro-4-methylbenzofuran (5).
Figure 4:
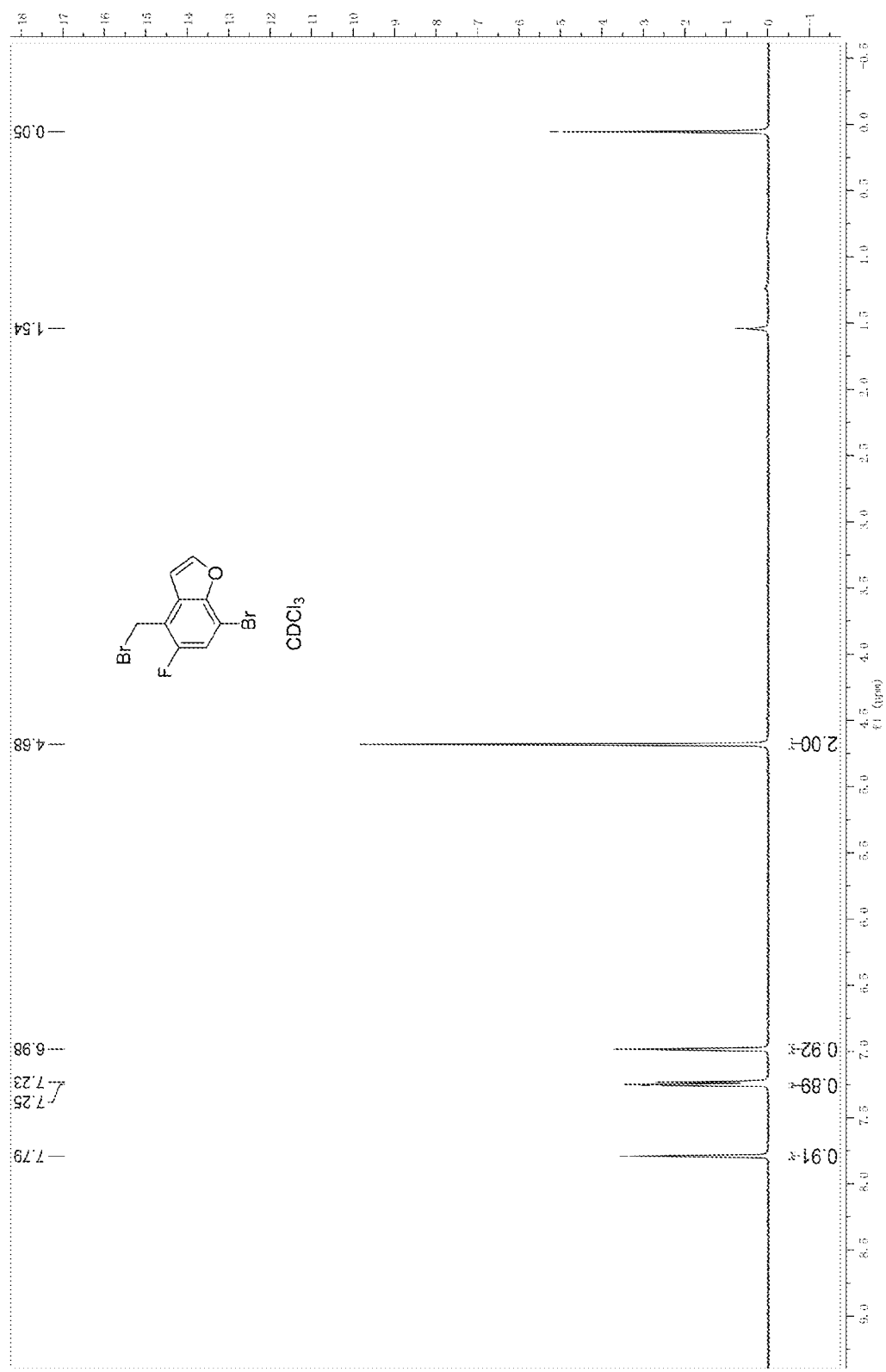
FIG. 4 shows the H-NMR spectrum of 7-bromo-4-(bromomethyl)-5-fluorobenzofuran (6).
Figure 5:
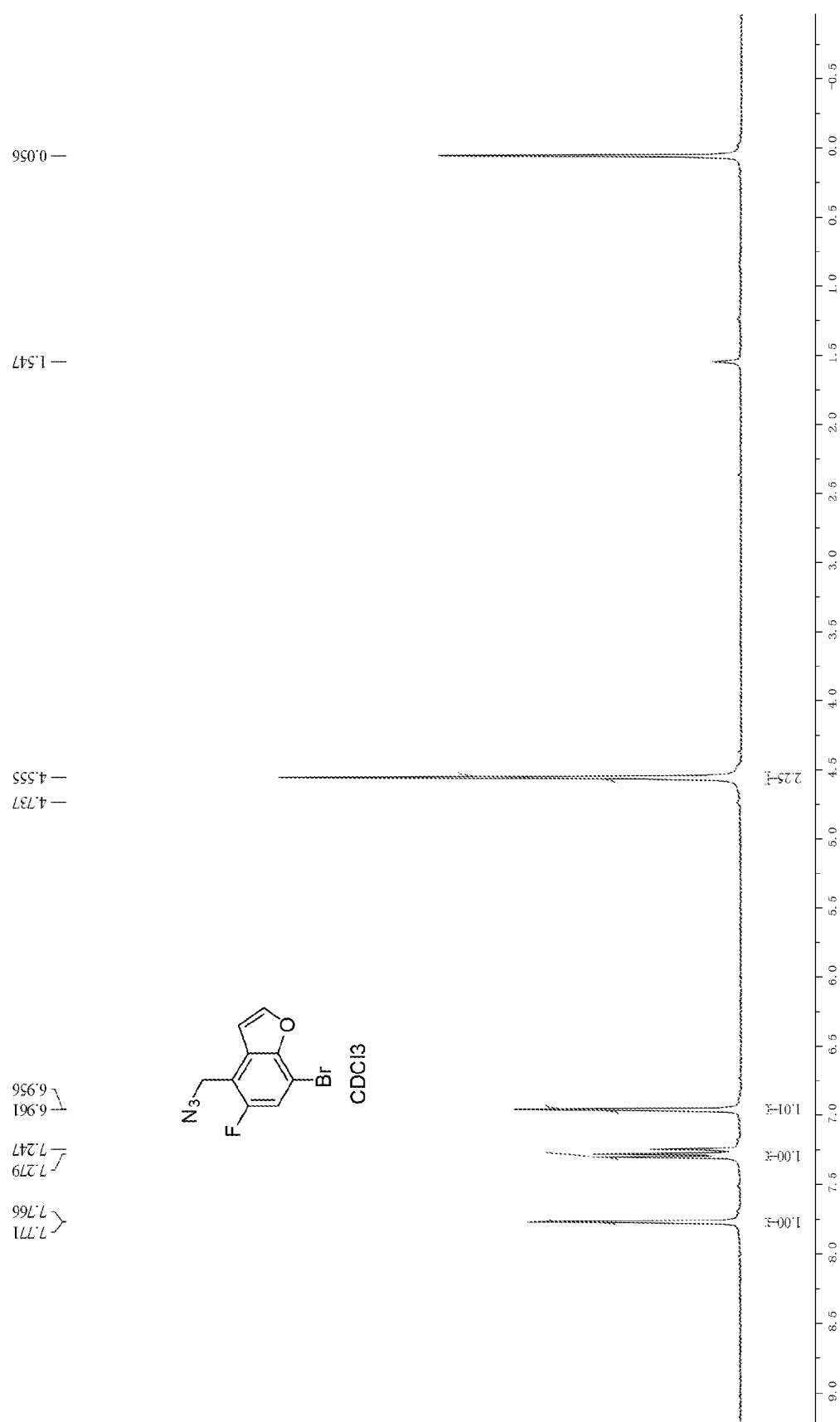
FIG. 5 shows the H-NMR spectrum of 7-bromo-5-fluoro-4-azidomethyl-benzofuran (7).
Figure 6:
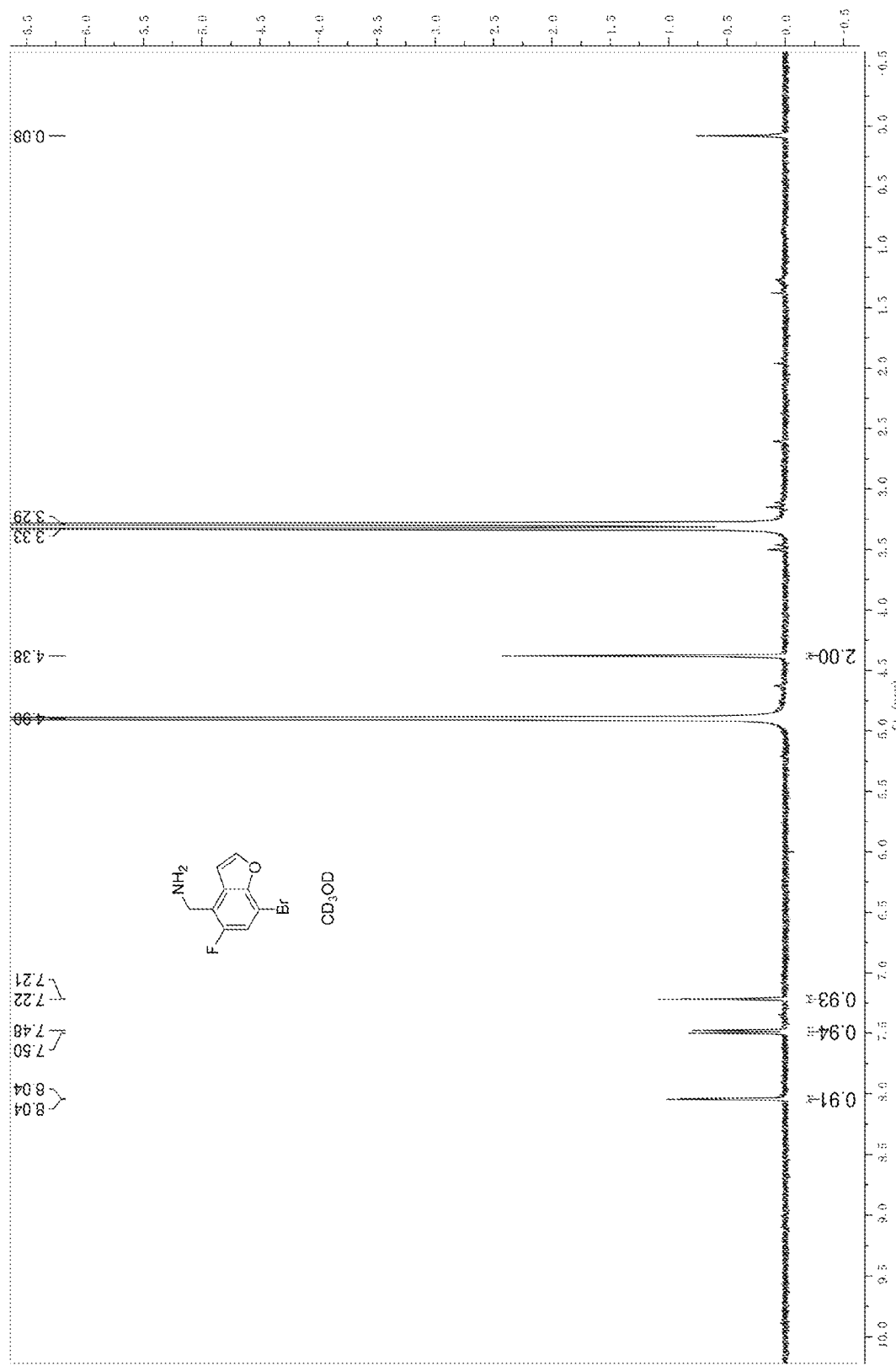
FIG. 6 shows the H-NMR spectrum of 7-bromo-4-(aminomethyl)-5-fluorobenzofuran (9).
Figure 7:
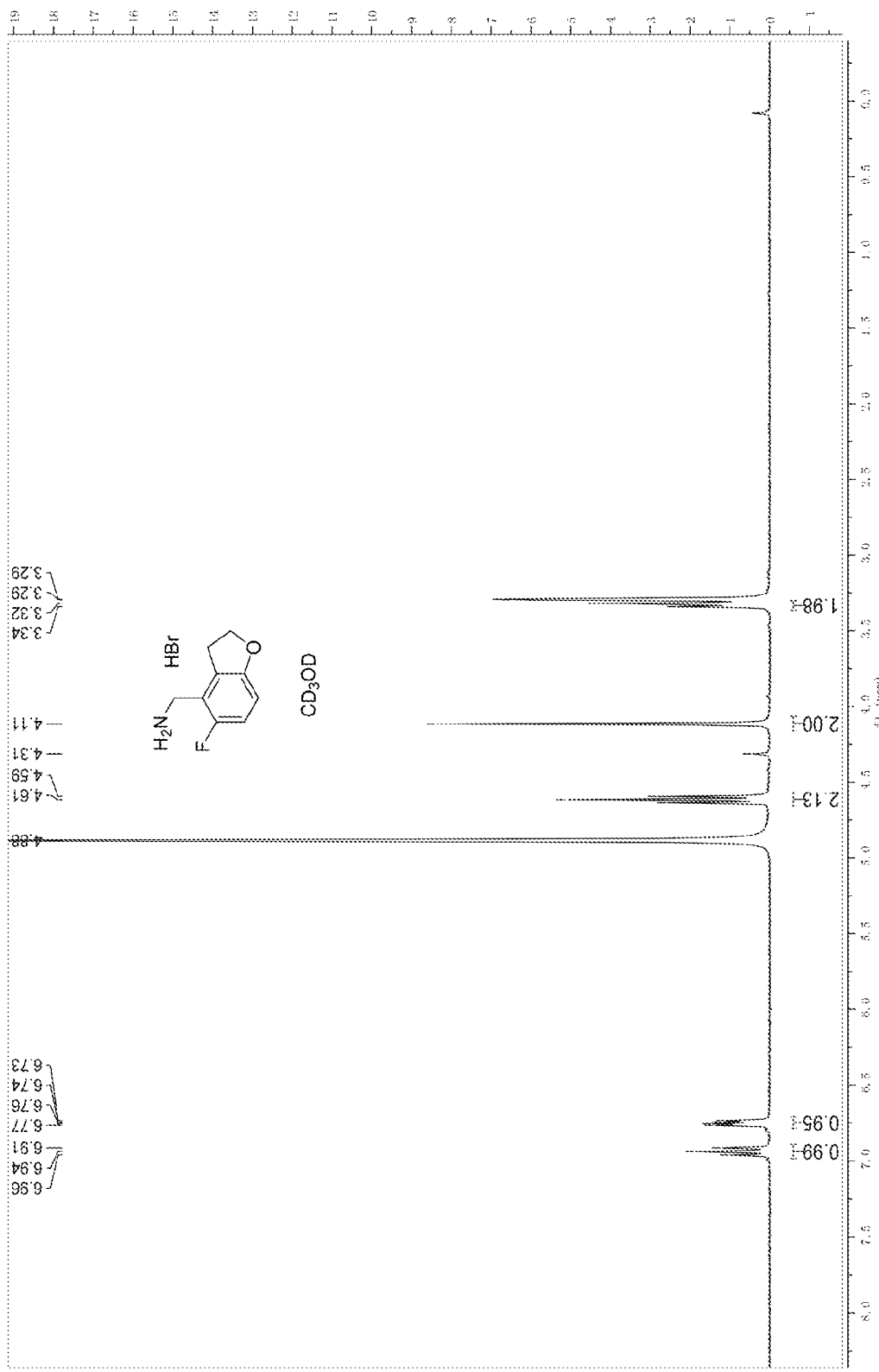
FIG. 7 shows the H-NMR spectrum of (5-fluoro-2,3-dihydrobenzofuran-4-yl)methylamine (8) hydrobromide.

The specific details of the preparation method of the present invention are illustrated in the following sections. It should be understood that, the illustrative description is only to facilitate those skilled in the art to better understand and practice the present invention, and does not constitute any limitation on the protection scope of the present invention. Those skilled in the art can adjust and/or modify one or more details in combination with the conventional practice in the chemical field, and the technical solutions after the adjustment and/or modification also fall within the scope of the present invention.

In one aspect, the present invention provides a preparation method of (5-fluoro-2,3-dihydrobenzofuran-4-yl)methylamine or a salt thereof, which comprises the following reaction steps:

1) Taking 4-fluoro-3-methylphenol (1) as the starting material, and brominating it to obtain 2-bromo-4-fluoro-5-methylphenol (2);

2) Performing 0-alkylation reaction between 2-bromo-4-fluoro-5-methylphenol (2) and 2-bromo-1,1-diethoxyethane (3) to obtain 1-bromo-2-(2,2-diethoxyethoxy)-5-fluoro-4-toluene (4);

3) Cyclizing 1-bromo-2-(2,2-diethoxyethoxy)-5-fluoro-4-toluene (4) to obtain 7-bromo-5-fluoro-4-methylbenzofuran (5);

4) Brominating 7-bromo-5-fluoro-4-methylbenzofuran (5) to obtain 7-bromo-4-(bromomethyl)-5-fluorobenzofuran (6);

5) Preparing (5-fluoro-2,3-dihydrobenzofuran-4-yl)methylamine or a salt thereof using the following two-step reaction in any one of 5.1 or 5.2:

5.1) Aziding 7-bromo-4-(bromomethyl)-5-fluorobenzofuran (6) in the presence of an azide to obtain 7-bromo-5-fluoro-4-azidomethyl-benzofuran (7), which is then hydrogenated to obtain (5-fluoro-2,3-dihydrobenzofuran-4-yl)methylamine (8) or a salt thereof; or 5.2) Ammonolyzing 7-bromo-4-(bromomethyl)-5-fluorobenzofuran (6) to obtain 7-bromo-4-(aminomethyl)-5-fluorobenzofuran (9), which is then hydrogenated to obtain (5-fluoro-2,3-dihydrobenzofuran-4-yl)methylamine (8) or a salt thereof.

Hereinafter, each step will be illustrated with reference to the above Scheme 1 and the preparation method.

Step 1)

4-fluoro-3-methylphenol is mixed with a reaction solvent and the temperature is lowered to −70° C. to −40° C. A bromination reagent is slowly added dropwise, and the dropping time is controlled within 1-2 h to prevent the rapid dropping rate from producing polysubstituted bromide, and the reaction system is monitored after the dropwise addition is over. After the reaction is over, the unreacted bromination reagent can be treated by adding at least one of saturated sodium thiosulfate and water, saturated sodium thiosulfate and saturated sodium bicarbonate, and saturated sodium bisulfite and water, or a mixture thereof, and then adding dichloromethane, and adopting the conventional post-treatment method in the art.

In one embodiment, the bromination reagent is selected from at least one of bromine, phosphorus oxybromide, phosphorus pentabromide, phosphorus tribromide, dibromotrialkylphosphine, dibromodiphenylphosphine, NBS, and dibromohydantoin; preferably bromine, phosphorus oxybromide, and NBS.

In one embodiment, the molar ratio of 4-fluoro-3-methylphenol to the bromination reagent is 1:(1-2), more preferably 1:(1-1.5).

In one embodiment, the reaction solvent is selected from at least one of chlorinated alkanes, ethers, $C_1$-$C_4$ alcohols, acetonitrile, and DMF, preferably chlorinated alkanes, and more preferably dichloromethane, chloroform, and dichloroethane.

In one embodiment, the reaction time is preferably 1-5 h, more preferably 1-2 h.

Step 2)

A reaction solvent, 2-bromo-4-fluoro-3-methylphenol, 2-bromo-1,1-diethoxyethane and a base are mixed to perform the O-alkylation reaction. The reaction system is heated to 70-150° C., and the reaction time is 1-20 h. After the reaction is over, the reaction system is monitored, and water and methyl tert-butyl ether are sequentially added, and a conventional post-treatment method in the art is adopted for the treatment.

In one embodiment, the molar ratio of 2-bromo-4-fluoro-3-methylphenol to 2-bromo-1,1-diethoxyethane is 1:(1-2), more preferably 1:(1-1.5).

In one embodiment, the molar ratio of 2-bromo-4-fluoro-3-methylphenol to the base is 1:(1-3), more preferably 1:(1-2).

In one embodiment, the base is selected from inorganic base or organic base, and the inorganic base is selected from at least one of sodium hydroxide, potassium hydroxide, sodium carbonate, potassium carbonate, sodium bicarbonate, and potassium bicarbonate, and the organic base is selected from at least one of pyridine, triethylamine, diisopropylethylamine, potassium tert-butoxide, sodium tert-butoxide, sodium methoxide, sodium ethoxide, and DBU, or a mixture thereof.

In one embodiment, the reaction solvent is selected from at least one of DMF, acetonitrile, DMSO, toluene, or xylene, or a mixture thereof.

In one embodiment, the reaction temperature is preferably 80-120° C., and the reaction time is preferably 10-20 h.

Step 3)

Polyphosphoric acid (PPA) and a reaction solvent are heated to 50-120° C., and a mixture system of 1-bromo-2-(2,2-diethoxyethoxy)-5-fluoro-4-toluene and a reaction solvent is slowly added dropwise. The reaction system is heated to 50-120° C. and the reaction time is 1-20 h. After the reaction is over, the reaction system is monitored, water and hexane are added sequentially, and a conventional post-treatment method in the art is adopted for the treatment.

In one embodiment, the molar ratio of 1-bromo-2-(2,2-diethoxyethoxy)-5-fluoro-4-toluene to PPA is 1:(1-5), preferably 1:(1-2).

In one embodiment, the reaction solvent is at least one of toluene and xylene, or a mixture thereof.

In one embodiment, the reaction temperature is preferably 50-100° C., and the reaction time is preferably 10-20 h.

Step 4)

7-bromo-5-fluoro-4-methylbenzofuran, a reaction solvent, a peroxide initiator and a bromination reagent are added sequentially, and the reaction system is heated to 50-120° C. and reacted for 1-20 h in an inert environment. After the reaction is over, the reaction system is monitored, water and ethyl acetate are added, and a conventional post-treatment method in the art is adopted for the treatment.

In one embodiment, the reaction solvent is selected from at least one of chlorinated alkanes, ethers, $C_1$-$C_4$ alcohols, acetonitrile, ethyl acetate, and DMF; more preferably dichloromethane, chloroform, dichloroethane, carbon tetrachloride, and ethyl acetate.

In one embodiment, the peroxide initiator is selected from at least one of acyl peroxides, hydroperoxides, dialkyl peroxides, and peroxide-esters, and is more preferably selected from benzoyl peroxide, lauroyl peroxide, cumyl hydroperoxide, tert-butyl hydroperoxide, di-tert-butyl peroxide, dicumyl peroxide, tert-butyl peroxybenzoate; and tert-butyl peroxypivalate In one embodiment, the bromination reagent is selected from at least one of bromine, phosphorus oxybromide, phosphorus pentabromide, phosphorus tribromide, dibromotrialkylphosphine, dibromodiphenylphosphine, NBS, and dibromohydantoin; preferably bromine, NBS and dibromohydantoin.

In one embodiment, the inert environment is selected from nitrogen and argon.

In one embodiment, the molar ratio of 7-bromo-5-fluoro-4-methylbenzofuran to the peroxide initiator is 1:(0.1-0.5), more preferably 1:(0.1-0.3).

In one embodiment, the molar ratio of 7-bromo-5-fluoro-4-methylbenzofuran to the brominating reagent is 1:(1-2), more preferably 1:(1-1.5).

In one embodiment, the reaction temperature is preferably 80-120° C., and the reaction time is preferably 10-20 h.

Step 5.1) Azidation

Water, an azide and a reaction solvent are added sequentially, and stirred evenly at 20-50° C., 7-bromo-4-(bromomethyl)-5-fluorobenzofuran is gradually add, and stirred at 20-25° C. for 1-20 h. After the reaction is over, the reaction system is monitored, water and methyl tert-butyl ether are added, and a conventional post-treatment method in the art is adopted for the treatment.

In one embodiment, the azide is selected from sodium azide and potassium azide.

In one embodiment, the molar ratio of 7-bromo-4-(bromomethyl)-5-fluorobenzofuran to the azide is 1:(1-2), more preferably 1:(1-1.5).

In one embodiment, the reaction temperature is 20-80° C., and the reaction time is 10-20 h.

In one embodiment, the reaction solvent is at least one of chlorinated alkanes, ethers, $C_1$-$C_4$ alcohols, acetonitrile, DMF, ethyl acetate, DMSO, and ketone solvents; more preferably DMF, acetonitrile, acetone, 2-methylbutanone.

Step 5.1) Hydrogenation

In an autoclave, a reaction solvent, a catalyst and 7-bromo-5-fluoro-4-azidomethyl-benzofuran are sequentially added. After nitrogen replacement, the hydrogen gas is pressurized to 0.2-3 Mpa, and the reaction is heated to 40-100° C. for 24-48 h. After the reaction is over, the reaction system is monitored, the catalyst is filtered, and a conventional post-treatment method in the art is adopted for the treatment.

In one embodiment, the reaction solvent is selected from common solvents such as $C_1$-$C_4$ alcohols, ethers, chlorinated alkanes; and more preferably methanol, ethanol.

In one embodiment, the catalyst is selected from a palladium catalyst or Raney nickel, more preferably a palladium catalyst, and the mass ratio of 7-bromo-5-fluoro-4-azidomethyl-benzofuran to the catalyst is (10-20):1, more preferably 10:1.

Step 5.2) Aminolysis 7-bromo-4-bromomethyl-5-fluorobenzofuran is dissolved in tetrahydrofuran and the resulting solution is dropped into a homemade or commercially available high-concentration ammonia-methanol solution at −20° C. The system is sealed and reacted under stirring.

In one embodiment, the reaction temperature is room temperature or ambient temperature, and the reaction time is 1-48 h.

Step 5.2) Hydrogenation

In an autoclave, a reaction solvent, a catalyst and 7-bromo-4-(aminomethyl)-5-fluorobenzofuran are sequentially added. After nitrogen replacement, the hydrogen gas is pressurized to 0.2-3 Mpa, and the reaction is heated to 40-100° C. for 24-48 h. After the reaction is over, the reaction system is monitored, the catalyst is filtered, and a conventional post-treatment method in the art is adopted for the treatment.

In one embodiment, the reaction solvent is selected from common solvents such as $C_1$-$C_4$ alcohols, ethers, chlorinated alkanes; and more preferably methanol, ethanol.

In one embodiment, the catalyst is selected from a palladium catalyst or Raney nickel, more preferably a palladium catalyst, and the mass ratio of 7-bromo-4-(aminomethyl)-5-fluorobenzofuran to the catalyst is (10-50):1, more preferably 10:1.

EXAMPLES

In the following examples, the compounds used were commercially available or obtained by self-made methods.

Example 1

Synthesis of 2-bromo-4-fluoro-5-methylphenol (2)

The solution of 4-fluoro-3-methylphenol (400 g, 3.17 mol) in 8L of dichloromethane was cooled to −70 ° C., and kept at −60 ° C., and $Br_2$ (527 g, 3.33 mol) was added dropwise. The reaction lasted for 2 hours, and the reaction was monitored and no reaction material remained. 1 L of saturated $Na_2S_2O_3$ solution and 3L of water were added, and the reaction liquid was slowly warmed to room temperature and separated. The aqueous phase was extracted with dichloromethane (1L*2), and the organic layers were combined. After post-treatment and concentration, 705 g of product was obtained, which was slurried with n-hexane to obtain 533 g of product with a yield of 82%.

Nuclear magnetic data: $^1$H NMR (300 MHz, $CDCl_3$, ppm): δ7.10 (d, 1H), 6.82 (d, 1H), 2.19 (s, 3H).

Example 2

Synthesis of 1-bromo-2-(2,2-diethoxyethoxy)-5-fluoro-4-toluene (4)

To a solution of 2-bromo-4-fluoro-3-methylphenol (530 g, 2.59 mol) in 2L of DMF was added potassium carbonate (713 g, 5.17 mol) and 2-bromo-1,1-diethoxy ethane (662 g, 3.36 mol). The mixture was heated to 120° C. and reacted for 16 h. The reaction was monitored and no reaction material remained. The reaction was cooled to room temperature; the mixture was poured into 5L of water, and then extracted with methyl tert-butyl ether (4L*3). The combined organic phase was washed with 4L of water and 4L of brine, dried and concentrated to obtain 902 g of crude product.

Nuclear magnetic data: $^1$H NMR (300 MHz, CDCl$_3$, ppm): δ 7.16 (d, 1H), 6.70 (d, 1H), 4.82 (t, 1H), 3.96 (d, 2H), 3.79 (m, 2H), 3.54 (m, 2H), 2.18 (s, 3H), 1.21 (t, 6H).

Example 3

Synthesis of 7-bromo-5-fluoro-4-methylbenzofuran (5)

The mixture of polyphosphoric acid (1893 g, 5.60 mol) in 3L of toluene was heated to 90° C., and the solution of 1-bromo-2-(2,2-diethoxyethoxy)-5-fluoro-4-toluene (900 g, 2.80 mol) in 600 ml of toluene was added dropwise. The reaction was heated to 100° C. for 16 h. The reaction was monitored and no reaction material remained. The reaction was then cooled to room temperature and poured into 5L of water, and extracted with n-hexane (4L*3). The combined organic phase was washed with 4L of water and 4L of brine, dried and concentrated to obtain 700 g of crude product, which was then mixed with 800 g of silica gel and washed with petroleum ether to obtain 320 g of product, and the two-step yield of Examples 2-3 was 54%.

Nuclear magnetic data: $^1$H NMR (300 MHz, CDCl$_3$, ppm): δ7.67 (s, 1H), 7.16 (d, 1H), 6.81 (s, 1H), 2.35 (s, 3H).

Example 4

Synthesis of 7-bromo-4-(bromomethyl)-5-fluorobenzofuran (6)

7-bromo-5-fluoro-4-methylbenzofuran (320 g, 1.40 mol), 6.5L of ethyl acetate, and then benzoyl peroxide (33.9 g, 0.14 mol) and NBS (324 g, 1.82 mol) were added sequentially. The flask was ventilated 3 times, then heated to 80° C. and reacted under nitrogen for 20 hours. The reaction was monitored and no reaction material remained. The reaction was cooled to room temperature, and poured into 3L of water. The organic phase was separated, and the aqueous phase was extracted with ethyl acetate (2L*2). The combined organic phase was washed with 3L of water and 3L of brine, dried and concentrated to obtain 580 g of crude product, which was refined with methanol-n-hexane to obtain 320 g of product, with a yield of 74%.

Nuclear magnetic data: $^1$H NMR (300 MHz, CDCl$_3$, ppm): δ 7.79 (s, 1H), 7.23 (d, 1H), 6.98 (s, 1H), 4.68 (s, 2H).

Example 5

Synthesis of 7-bromo-5-fluoro-4-azidomethylbenzofuran (7)

0.96 L of water, 81.3 g of sodium azide (1.25 mol, 1.2 eq) and 1.92 L of acetone were added sequentially. The mixture was stirred at room temperature, and 7-bromo-4-(bromomethyl)-5-fluorobenzofuran (320 g, 1.04 mol) was gradually added. The reaction was stirred at room temperature for 18 hours. The reaction was monitored and no reaction material remained. The reaction was added with 2L of water, and extracted with methyl tert-butyl ether (3L*3). The combined organic phase was washed with water and brine, dried and concentrated to obtain 265 g of product with a yield of 94%.

Nuclear magnetic data: $^1$H NMR (300 MHz, CDCl$_3$, ppm): δ7.77 (s, 1H), 7.28 (d, 1H), 6.96 (s, 1H), 4.56 (s, 2H).

Example 6

Synthesis of (5-fluoro-2,3-dihydrobenzofuran-4-yl)methylamine (8)

1L of methanol, 17 g of 10% Pd/C, and 170 g of 7-bromo-5-fluoro-4-azidomethylbenzofuran were added to an autoclave. After nitrogen replacement three times, the hydrogen gas was pressurized to 3 Mpa. The mixture was heated to 60° C. and reacted for 48 hours. After the reaction was over, the catalyst was filtered, and the filtrate was concentrated to obtain 156 g of product in the form of hydrobromide, with a yield of 92%.

Nuclear magnetic data: $^1$H NMR (300 MHz, CDCl$_3$, ppm): δ 6.94 (t, 1H), 6.74 (dd, 1H), 4.59 (t, 2H), 4.11 (s, 2H), 3.29 (t, 2H).

Example 7

Synthesis of 7-bromo-4-(aminomethyl)-5-fluorobenzofuran (9)

13.0 g of 7-bromo-4-bromomethyl-5-fluorobenzofuran was dissolved in 35 ml of tetrahydrofuran and the resulting solution was dropped into 10N ammonia-methanol solution. After the addition, the reaction liquid was sealed and stirred overnight at room temperature, and concentrated. The crude product was slurried with 100 ml of ethyl acetate, filtered, and dried to obtain 10.2 g of white solid product with a yield of 75%.

Nuclear magnetic data: $^1$H NMR (300 MHz, CDCl$_3$, ppm): δ8.05 (d, 1H), 7.48 (d, 1H), 7.25 (d, 2H), 4.40 (s, 2H).

Example 8

Synthesis of (5-fluoro-2,3-dihydrobenzofuran-4-yl)methylamine (8)

Reference is made to the operation in Example 6 for pressurized hydrogenation to obtain the product.

Nuclear magnetic data: $^1$H NMR (300 MHz, CDCl$_3$, ppm): δ 6.94 (t, 1H), 6.74 (dd, 1H), 4.59 (t, 2H), 4.11 (s, 2H), 3.29 (t, 2H).

Each reference document, including all patents, patent applications, and publications cited in the present application, is incorporated herein by reference in its entirety, as if each of them was individually incorporated. In addition, it would be understood that, with the above teachings of the present invention, those skilled in the art could make certain changes or modifications to the present invention, and these equivalents will still fall within the scope of the present invention defined by the appended claims of the application.

What is claimed is:

1. A method of preparing (5-fluoro-2,3-dihydrobenzofuran-4-yl) methylamine or a salt thereof, which comprises the following reaction steps:
   1) Brominating 4-fluoro-3-methylphenol as the starting material to obtain 2-bromo-4-fluoro-5-methylphenol;
   2) Performing O-alkylation reaction between 2-bromo-4-fluoro-5-methylphenol and 2-bromo-1, 1-diethoxyethane to obtain 1-bromo-2-(2,2-diethoxyethoxy)-5-fluoro-4-toluene;
   3) Cyclizing 1-bromo-2-(2,2-diethoxyethoxy)-5-fluoro-4-toluene to obtain 7-bromo-5-fluoro-4-methylbenzofuran;

4) Brominating 7-bromo-5-fluoro-4-methylbenzofuran to obtain 7-bromo-4-(bromomethyl)-5-fluorobenzofuran; and 5) Preparing (5-fluoro-2,3-dihydrobenzofuran-4-yl) methylamine or a salt thereof using the following two-step reaction in 5.1 or 5.2:

5.1) Aziding 7-bromo-4-(bromomethyl)-5-fluorobenzofuran in the presence of an azide to obtain 7-bromo-5-fluoro-4-azidomethyl-benzofuran, which is then hydrogenated to obtain (5-fluoro-2,3-dihydrobenzofuran-4-yl) methylamine or a salt thereof; or 5.2) Ammonolyzing 7-bromo-4-(bromomethyl)-5-fluorobenzofuran to obtain 7-bromo-4-(aminomethyl)-5-fluorobenzofuran, which is then hydrogenated to obtain (5-fluoro-2,3-dihydrobenzofuran-4-yl) methylamine or a salt thereof.

2. The method of claim 1, wherein step 1) is carried out by slowly adding a bromination reagent dropwise to a mixture of 4-fluoro-3-methylphenol and a reaction solvent, and optionally has one or more of the following features:
the reaction temperature is −78° C. to −10° C.;
the bromination reagent is selected from at least one of bromine, phosphorus oxybromide, phosphorus pentabromide, phosphorus tribromide, dibromotrialkylphosphine, dibromodiphenylphosphine, NBS, and dibromohydantoin;
the molar ratio of 4-fluoro-3-methylphenol to the bromination reagent is 1: (1-2);
the reaction solvent is selected from at least one of chlorinated alkanes, ethers, C1-C4 alcohols, acetonitrile, and DMF; and/or
the reaction time is 1-5 h.

3. The method of claim 1, wherein step 2) is carried out by performing O-alkylation reaction between 2-bromo-4-fluoro-5-methylphenol and 2-bromo-1,1-diethoxyethane in the presence of a base and a reaction solvent, and optionally has one or more of the following features:
the reaction temperature is 70-150° C.;
the molar ratio of 2-bromo-4-fluoro-3-methylphenol to 2-bromo-1,1-diethoxyethane is 1: (1-2);
the molar ratio of 2-bromo-4-fluoro-3-methylphenol to the base is 1: (1-3);
the base is selected from inorganic base or organic base, and the inorganic base is selected from at least one of sodium hydroxide, potassium hydroxide, sodium carbonate, potassium carbonate, sodium bicarbonate, and potassium bicarbonate; and the organic base is selected from at least one of pyridine, triethylamine, diisopropylethylamine, potassium tert-butoxide, sodium tert-butoxide, sodium methoxide, sodium ethoxide, and DBU;
the reaction solvent is selected from at least one of DMF, acetonitrile, DMSO, toluene or xylene; and/or
the reaction time is 1-20 h.

4. The method of claim 1, wherein step 3) is carried out by adding 1-bromo--(2,2-diethoxyethoxy)-5-fluoro-4-toluene dropwise to a mixture of polyphosphoric acid and a reaction solvent, and optionally has one or more of the following features:
the reaction temperature is 50-120° C.;
the molar ratio of 1-bromo-2-(2,2-diethoxyethoxy)-5-fluoro-4-toluene to polyphosphoric acid is 1: (1-5);
the reaction solvent is at least one of toluene and xylene; and/or
the reaction time is 1-20 h.

5. The method of claim 1, wherein step 4) is carried out by brominating 7-bromo-5-fluoro-4-methylbenzofuran in the presence of a reaction solvent, a peroxide initiator and a bromination reagent, and optionally has one or more of the following features:
the reaction temperature is 50-120° C.;
the reaction is carried out in an inert environment, and optionally the inert environment is selected from nitrogen or argon;
the reaction solvent is selected from at least one of chlorinated alkanes, ethers, $C_1$-$C_4$ alcohols, acetonitrile, ethyl acetate, and DMF;
the peroxide initiator is selected from at least one of acyl peroxides, hydroperoxides, dialkyl peroxides, and peroxide-esters, and is more preferably selected from benzoyl peroxide, lauroyl peroxide, cumyl hydroperoxide, tert-butyl hydroperoxide, di-tert-butyl peroxide, dicumyl peroxide, tert-butyl peroxybenzoate;, tert-butyl peroxypivalate;
the bromination reagent is selected from at least one of bromine, phosphorus oxybromide, pentabromide, phosphorus tribromide, dibromotrialkylphosphine, phosphorus dibromodiphenylphosphine, NBS, and dibromohydantoin;
the molar ratio of 7-bromo-5-fluoro-4-methylbenzofuran to the peroxide initiator is 1: (0.1-0.5);
the molar ratio of 7-bromo-5-fluoro-4-methylbenzofuran to the bromination reagent is 1: (1-2); and/or
the reaction time is 1-20 h.

6. The method of claim 1, wherein the azidation in step 5.1) is carried out by reacting an azide with 7-bromo-5-fluoro-4-methylbenzofuran in water and a reaction solvent, and optionally has one or more of the following features:
the reaction temperature is 20-80° C.;
the azide is selected from sodium azide or potassium azide;
the molar ratio of 7-bromo-5-fluoro-4-methylbenzofuran to the azide is 1: (1-2);
the reaction solvent is at least one of chlorinated alkanes, ethers, $C_1$-$C_4$ alcohols, acetonitrile, DMF, ethyl acetate, DMSO, and ketone solvents; and/or
the reaction time is 1-20 h.

7. The method of claim 1, wherein the hydrogenation in step 5.1) is carried out by hydrogenating 7-bromo-5-fluoro-4-azidomethyl-benzofuran under pressure in the presence of a catalyst, and optionally has one or more of the following features:
the hydrogen pressure is 0.2-3 Mpa;
the reaction temperature is 40-100° C.;
the reaction solvent is selected from $C_1$-$C_4$ alcohols, THF, chlorinated alkanes, and is more preferably selected from methanol or ethanol;
the catalyst is selected from at least one of palladium catalyst or Raney nickel;
the mass ratio of 7-bromo-5-fluoro-4-azidomethyl-benzofuran to the catalyst is (10-50): 1; and/or
the reaction time is 24-48 h.

8. The method of claim 1, wherein the ammonolysis in step 5.2) is carried out in an ammonia-alcohol solution, and optionally has one or more of the following features:
the reaction temperature is −30–25° C.;
the reaction solvent is selected from $C_1$-$C_4$ alcohols, and is more preferably selected from methanol or ethanol;
the ammonia concentration in the ammonia-alcohol solution is 5 N-10 N; and/or
the reaction time is 1-48 h.

9. The method of claim1, wherein the hydrogenation in step 5.2) is carried out by hydrogenating 7-bromo-4-(aminomethyl)-5-fluorobenzofuran under pressure in the presence of a catalyst, and optionally has one or more of the following features:

the hydrogen pressure is 0.2-3 Mpa;
    the reaction temperature is 40-100° C.;
    the reaction solvent is selected from $C_1$-$C_4$ alcohols, and is more preferably selected from methanol or ethanol;
    the catalyst is selected from at least one of palladium catalyst or Raney nickel;
    the mass ratio of 7-bromo-4-(aminomethyl)-5-fluorobenzofuran to the catalyst is (10-50): 1; and/or
    the reaction time is 24-48 h.

10. The method of claim1, wherein the salt of (5-fluoro-2,3-dihydrobenzofuran-4-yl) methylamine is hydrobromide.

11. An intermediate compound used for the preparation of (5-fluoro-2,3- dihydrobenzofuran-4-yl) methylamine or a salt thereof, which is selected from the group consisting of: 1-bromo-2-(2,2-diethoxyethoxy)-5-fluoro-4-toluene, 7-bromo-4-(bromomethyl)-5-fluorobenzofuran, 7-bromo-5-fluoro-4-azidomethyl benzofuran and 7-bromo-4-(aminomethyl)-5-fluorobenzofuran.

\* \* \* \* \*

UNITED STATES PATENT AND TRADEMARK OFFICE
CERTIFICATE OF CORRECTION

PATENT NO. : 12,221,427 B2
APPLICATION NO. : 17/425817
DATED : February 11, 2025
INVENTOR(S) : Qingquan Wu et al.

It is certified that error appears in the above-identified patent and that said Letters Patent is hereby corrected as shown below:

In the Claims

Column 12, Lines 56-57, Claim 1, replace:
"(5-fluoro-2,3-dihydrobenzo-furan-4-yl) methylamine"
With:
--(5-fluoro-2,3-dihydrobenzofuran-4-yl)methylamine--.

Column 13, Lines 4-5, Claim 1, replace:
"(5-fluoro-2,3-dihydrobenzofuran-4-yl) methylamine"
With:
--(5-fluoro-2,3-dihydrobenzofuran-4-yl)methylamine--.

Column 13, Lines 10-11, Claim 1, replace:
"(5-fluoro-2,3-dihydrobenzofuran-4-yl) methylamine"
With:
--(5-fluoro-2,3-dihydrobenzofuran-4-yl)methylamine--.

Column 13, Line 15, Claim 1, replace:
"(5-fluoro-2,3-dihydrobenzofuran-4-yl) methylamine"
With:
--(5-fluoro-2,3-dihydrobenzofuran-4-yl)methylamine--.

Column 13, Line 30, Claim 2, replace:
"C1-C4 alcohols,"
With:
--$C_1$-$C_4$ alcohols,--.

Signed and Sealed this
Twenty-third Day of December, 2025

John A. Squires
*Director of the United States Patent and Trademark Office*

Column 13, Lines 56-57, Claim 4, replace:
"1-bromo--(2,2-diethoxyethoxy)-5-fluoro-4-tolu-ene"
With:
--1-bromo-2-(2,2-diethoxyethoxy)-5-fluoro-4-toluene--.

Column 14, Line 20, Claim 5, replace:
"pentabromide,"
With:
--phosphorus pentabromide,--.

Column 14, Line 22, Claim 5, replace:
"phosphorus dibromodiphenylphosphine,"
With:
--dibromodiphenylphosphine,--.

At Column 15, Lines 13-14, Claim 10, replace:
"(5-fluoro-2,3-dihydrobenzofuran-4-yl) methylamine"
With:
--(5-fluoro-2,3-dihydrobenzofuran-4-yl)methylamine--.

At Column 15, Line 16, Claim 11, replace:
"(5-fluoro-2,3-dihydrobenzofuran-4-yl) methylamine"
With:
--(5-fluoro-2,3-dihydrobenzofuran-4-yl)methylamine--.